United States Patent [19]

Kratzer et al.

[11] Patent Number: 5,352,413
[45] Date of Patent: Oct. 4, 1994

[54] DEVICE FOR THE SAFE REMOVAL OF BLOOD FROM A SUPPLY VESSEL

[75] Inventors: Michael Kratzer, Munich; Volker F. von der Goltz, Seeon, both of Fed. Rep. of Germany

[73] Assignee: Baxter Diagnostics Inc., Deerfield, Ill.

[21] Appl. No.: 889,328

[22] Filed: Aug. 28, 1992

[30] Foreign Application Priority Data

May 28, 1991 [DE] Fed. Rep. of Germany ....... 4117483
Mar. 26, 1992 [DE] Fed. Rep. of Germany ....... 4209872

[51] Int. Cl.⁵ .................... B01L 3/02; G01N 33/00
[52] U.S. Cl. .................... 422/100; 422/73; 422/102; 422/103; 436/69; 73/64.41
[58] Field of Search ........... 422/99, 100, 102, 103, 422/73; 73/64.41; 436/69

[56] References Cited

U.S. PATENT DOCUMENTS

| | | | |
|---|---|---|---|
| 4,150,089 | 4/1979 | Linet | 422/102 |
| 4,604,894 | 8/1986 | Kratzer et al. | 422/73 X |
| 4,713,219 | 12/1987 | Gerken et al. | 422/102 |
| 4,808,381 | 2/1989 | McGregor et al. | 422/100 |
| 4,999,163 | 3/1991 | Lennon et al. | 422/102 X |
| 5,019,243 | 5/1991 | McEwen et al. | 422/101 X |
| 5,047,211 | 9/1991 | Sloane, Jr. et al. | 422/73 |
| 5,051,239 | 9/1991 | von der Goltz | 436/69 X |
| 5,089,422 | 2/1992 | Brubaker | 422/73 X |
| 5,211,310 | 5/1993 | Godolphin et al. | 422/100 X |

OTHER PUBLICATIONS

Scientific Products General Catalog—Baxter, 1991–92, p. 1818.

*Primary Examiner*—James C. Housel
*Assistant Examiner*—Maureen M. Wallenhorst
*Attorney, Agent, or Firm*—Louise S. Pearson

[57] ABSTRACT

The invention pertains to a device for the safe removal of blood from a supply vessel with an aperture holder in which a part having an aperture is held and to which a capillary is attached, whereby the supply vessel can be closed by a cover part. The cover part a region through which the capillary can be inserted into the supply vessel when the cover part is closed. Furthermore, the supply vessel and the aperture holder have a locking mechanism, so that the supply vessel can be locked to the aperture holder.

27 Claims, 3 Drawing Sheets

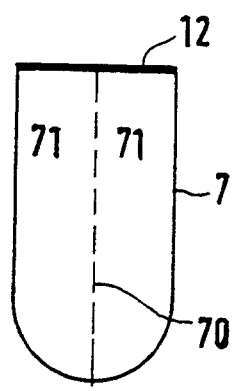
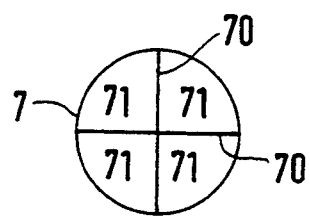
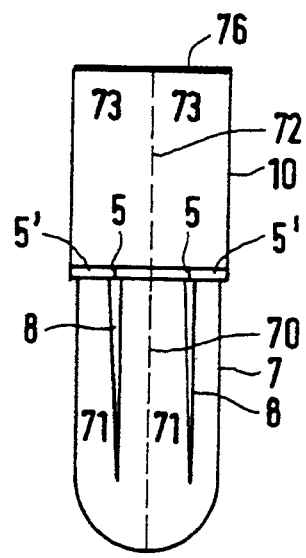
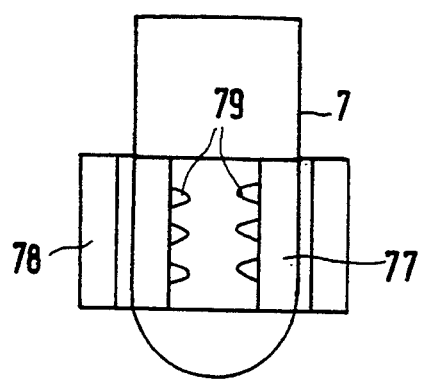

DEVICE FOR THE SAFE REMOVAL OF BLOOD FROM A SUPPLY VESSEL

FIELD OF THE INVENTION

The invention pertains to a device for the safe removal of blood from a supply vessel.

BACKGROUND OF THE INVENTION

As is known, according to FIG. 1, the bleeding time in vitro can be measured since blood 9 can be sucked from a supply vessel 7 via an aperture 5 into a cylinder 6, inasmuch as in the cylinder 6, a plunger 3 is moving by a stepping motor 2 in the direction 11. A pressure sensor 4 thereby measures the pressure prevailing in the chamber precircuited to plunger 3. This pressure will be held to a constant value such that a processor 1 drives the stepping motor 2 as a function of the signal of the pressure sensor 4. From the movement of the plunger and the diameter of the cylinder 6, the processor 1 computes the volume flow of the blood through the aperture 5. The aperture 5, whose diameter is at about 150 $\mu$m for example, simulates an injured portion of an arteriole. It is located for instance, in a cellulose acetate filter that is coated with collagen. The filter will be saturated with ADP (adenosine diphosphate) before the measurement. According to the described method, a reproducible measurement of the bleeding time in vitro and of the bleeding volume is possible.

Measurements of this type will be carried out in a measuring device inasmuch as a supply vessel for blood is inserted manually into the measuring device in a predetermined position; the seal of the supply vessel will be opened before carrying out the measurement, into the opened vessel, the capillary joined with an aperture holder will be inserted and a measuring head joined with the cylinder will be tightly connected to the side of the adapter holder turned away from the capillary.

One problem with measurements of this type consists in the fact that when handling the supply vessel and when installing the capillary into the supply vessel, contacts can occur with the blood located in the supply vessel, where said contacts must be avoided under all circumstances especially with regard to the transfer of AIDS or hepatitis. Contacts with the blood can also occur if the capillary is removed from the supply vessel after completion of the measurement.

The task of the present invention consists in specifying a device for the safe handling of a supply vessel for blood, with whose aid it is possible to avoid contacts with the blood contained in the supply vessel, both when opening the supply vessel, and also when inserting a capillary into the supply vessel.

BRIEF SUMMARY OF THE INVENTION

This problem is solved by a device of the type stated above, that is identified by the properties specified in the description below.

The essential advantage of the present invention consists in the fact that in the determination of the bleeding time in vitro, where blood is removed from a supply vessel via capillary, the potentials for contacts with the blood located in said supply vessel are essentially avoided. Thereby the transfer of extremely dangerous illnesses, like e.g. AIDS or hepatitis, can be avoided. This is an advantage of great significance in the performance of measurements in the laboratory or in hospitals, because the operating personnel performing the measurement are protected and because the work can be carried out simply and quickly as a result of the automatically increased safety, which leads to a savings in working time.

Preferably, contacts with the blood of the supply vessel will be avoided both upon insertion of the capillary jointed to the aperture holder into the supply vessel, and also upon removal of the capillary from the supply vessel.

In a preferred design, the adapter holder is joined to the side turned away from the measuring head, such that the exit of blood from the supply chamber of the adapter holder can not occur.

BRIEF DESCRIPTION OF THE DRAWINGS

The invention and its configurations will be explained in detail below in conjunction with the nonlimiting figures.

FIGS. 9 and 10 show supply vessels with several sub-chambers;

FIG. 11 shows the supply vessel of FIG. 9 with an aperture holder that is divided into two blood sampling chambers; and FIG. 12 shows an installation clip for reducing the volume of the supply vessel.

DETAILED DESCRIPTION OF THE DRAWINGS

Figure 2A:
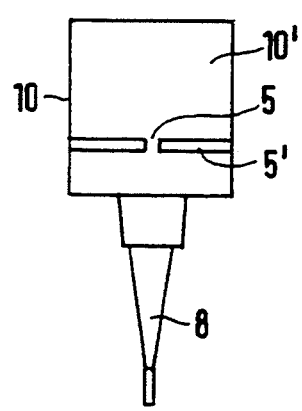
FIGS. 2a and 2b shows the capillary joined with the aperture holder and also a supply vessel located underneath, that is sealed by a cover.
Figure 2B:
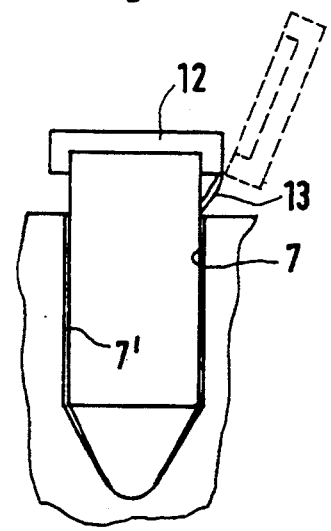

From FIG. 2, it is evident that the aperture holder 10 is designed together with the capillary 8, preferably as a single part that is made of disposable plastic. In the aperture holder 10, as is shown schematically, a part 5' having the aperture 5 is held in such a manner that blood sucked through the capillary 8 is fed to the aperture 5. Above the part 5' there is a supply chamber 10' holding the blood passing through the aperture 5. Now as part 5', we can use for example, a cellulose acetate filter coated with collagen.

In the manner illustrated in FIG. 2, the supply vessel 7 has preferably the shape of a cylindrical vessel sealed on one end, whose other end can be tightly sealed by means of a cover piece 12. Preferably the cover piece 12 is joined as a single piece with the supply vessel 7, both of which are made of a plastic material, by means of a so-called film hinge 13, so that the cover part 12 can not be detached from the supply vessel 7. Now in the handling of a supply vessel 7 filled with blood 9, we proceed such that the supply vessel 7 is installed into a holding trough or casing 7' underneath the measuring head of the measuring device. In this procedure, the supply vessel 7 is adjusted with respect to the measuring head. Before this installation, the supply vessel 7 is inverted repeatedly to mix up the blood 9, and thereafter the blood is incubated for about 4 minutes, whereby it is heated up to about 37° C. and then inverted once again. After installation into the holding casing 7', normally the cover piece 12 is opened manually and the capillary 8 is inserted into the supply vessel 7. And then, the measuring head is pressed from above, against the aperture holder 10.

Figure 3A:
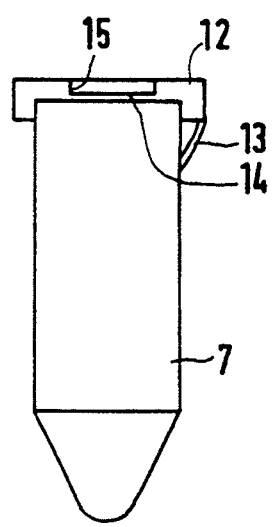
FIGS. 3a and 3b show a side view of a first sample design of the supply vessel, and, a top view of the cover of this supply vessel.

Now in order to avoid the danger of contact with the blood 9 located in the supply vessel in this procedure, the cover part 12 of the supply vessel 7 is designed so that the capillary 8 can be introduced into the supply vessel 7, without having to open the cover part 12. For this purpose, the cover part 12 can have the shape of a weak point or of a thin membrane 14, at least in one partial region as per FIGS. 3a, b where said weak place can be penetrated or pierced by a special tool or by the point of the capillary 8. Preferably, the named weak place 14 will have the shape of a cross slit 15 or of a central region 15', that is particularly easy to pierce. In this manner it is possible to avoid having to open the cover part 12 after installing the supply vessel 7 into the holding casing 7'.

Figure 4A:
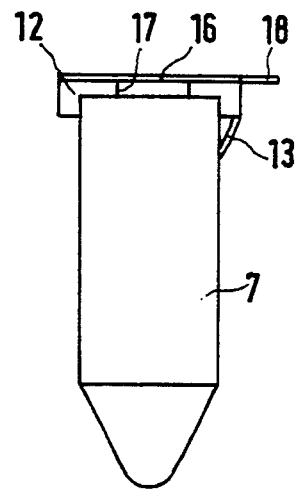
FIGS. 4a and 4b show a side view of a second design of the supply vessel, and also a top view of the cover of said supply vessel.

According to FIGS. 4a, b, the cover part 12 can also have an opening 17, sealed by a foil, preferably an adhesive foil 16 or such, whereby the adhesive foil 16 is located preferably on the outer side of the cover part 12 by means of the opening 17. Now preferably the adhesive foil 16 will have a grasping area 18 that will protrude out beyond the edge of the cover part 12, in order to allow an easier removal of the adhesive foil 16.

Figure 4B:
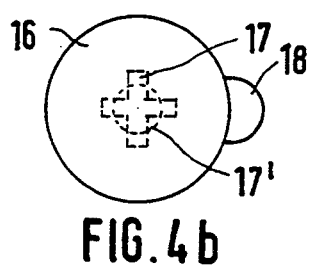

The opening 17 can have the shape of a cross slit, in the manner illustrated in FIG. 4b. For example, the opening 17 can also have the shape of a central hole, as is illustrated in FIG. 4b by the dashed line.

Figure 5:
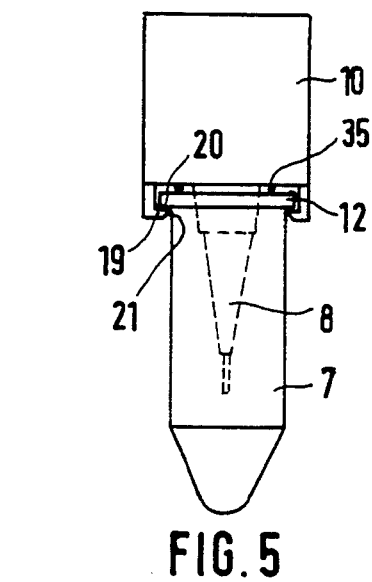
FIG. 5 shows a first type of locking mechanism of the supply vessel to the aperture holder.

To further increase the safety in the handling of the supply vessel 7 and of the aperture holder 10 with the capillary 8, both the supply vessel 7 and also the aperture holder 10 have locking mechanisms in the regions facing each other; this then causes the supply vessel 7 after insertion of the capillary 8 through the cover part 12, to be locked together, if for example, the measuring head of the measuring device presses the aperture holder 10 against the supply vessel 7. To do this, the aperture holder 10 has on its side facing the supply vessel 7, for example, several locking protrusions 19 distributed along its perimeter, that grasp behind a locking shoulder 20, that is formed by the transition between the cover part 12 set onto the supply vessel 7, and the perimeter of the supply vessel 7 (FIG. 5). In order to achieve a particularly easy springing of the locking protrusions 19, they can have so-called retraction slants 21 on the side facing the supply vessel 7, which will mean that the locking protrusions 19 are pressed spring-like outward, when the cover part 12 is pressed against them. This type of retraction slant can also be provided at the upper edge of the cover part 12.

Figure 6:
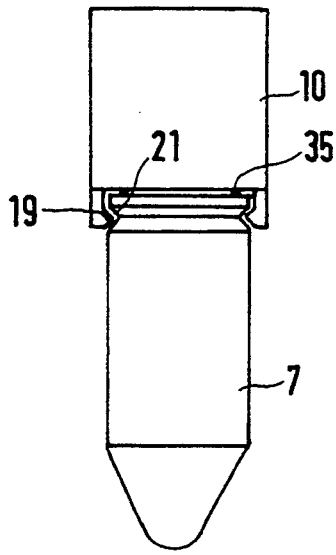
FIG. 6 shows a second type of locking mechanism of the supply vessel to the aperture holder.

According to FIG. 6, the locking features, stated generally, can be made of a locking protrusion 19 and a locking recess 21, whereby the locking protrusion 19 is provided at the aperture holder 10 (or the supply vessel or the cover part) and the locking recess 21 at the supply vessel 7 or the cover part 12 (or at the aperture holder).

Figure 7:
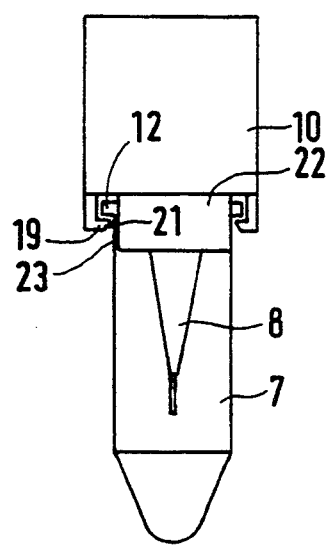
FIG. 7 shows an additional sample design of the invention.
Figure 3B:
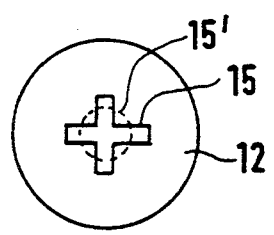

Particularly preferred is a design where the aperture holder 10 as per FIG. 7, has a stopper-like sealing region 22, that is inserted into the upper, end-region of the supply vessel 7 when setting the supply vessel 7 into the aperture holder 10, in order to seal it, so that when in a slant position, no blood can exit. Now in order to allow the inlet of air into the supply vessel 7 during the measuring operation and the removal of blood, care is taken that a ventilation gap 23 is provided between the sealing region 22 and the upper wall of the supply vessel 7, and said gap extends at least over a partial region of the perimeter of the supply vessel 7 and of the sealing region 22, via which the interior of the supply vessel 7 is in connection with the outside air. The ventilation gap 23 is sized preferably so that no blood can pass through it, since blood entering into the ventilation gap will cause it to plug up. For example, this ventilation gap will be on the order of 100 μm.

In this case, the cover part 12 of the supply vessel 7 is designed preferably as per FIG. 4, whereby the central opening (dashed line in FIG. 4b) is sized so that its edge regions do not extend inward over the edge regions of the supply vessel 7. In the case of a supply vessel 7 with a circular diameter, the diameter of the central opening of the cover piece 12 is slightly larger than the inner diameter of the supply vessel 7, so that the sealing region 22 can be inserted into the supply vessel 7 after pulling off the adhesive foil 18.

Figure 8:
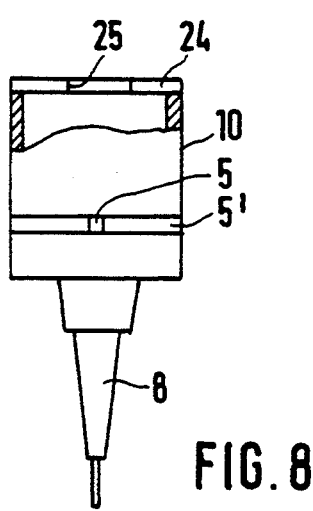
FIG. 8 shows an aperture holder whose side facing the measuring head is sealed by a foil having an opening.

As per FIG. 8, the end of the aperture holder 10 turned toward the test head can also be sealed by a part 24 that contains a central hole 25 through which the e.g. ADP can be inserted into the aperture holder 10, so that it can penetrate into the porous material of a part 5' held in the aperture holder 10 having the aperture 5. The member 24 has preferably the form of an adhesive foil joined to the aperture holder 10. By means of the membrane 24, any blood passing through the aperture 5 during the measurement operation is prevented from exiting from the aperture holder 10 in a slant position of said aperture holder, that might occur in the removal of the aperture holder 10 and of the supply vessel 7 preferably joined to it.

The foil 16 of FIGS. 4a, b, can have an extremely small adhesion factor, so that when pulling off the foil, no blood can hang on. It is possible to provide a sealing element 35 between the aperture holder 10 and the supply vessel 7 (FIGS. 5, 6) through which a tight joint is achieved between parts 10 and 7.

Now as is evident from FIGS. 9 and 10, the supply vessel 7 can be subdivided by one or more separator walls 70 into two or more chambers 71. Now care must be taken that the separator walls 70 extend upward toward the open side of the vessel, as high as the wall of the supply vessel 7. Now the cover part 12 sealing off the supply vessel 7, is configured so that it has a region for each chamber 71, through which a capillary can be inserted into the corresponding chamber 71. Now the region can be configured in the manner described above.

It is also possible to configure the cover part 12 in the form of an elastic membrane, whereby the points of the capillaries can produce a hole in this membrane; after pulling out the capillary, this hole will close automatically due to the elasticity of the material of the membrane. For this type of elastic membrane, it is also assured that in the locking of the aperture holder 10 to the supply vessel as per FIGS. 5, 6 and 7, the edge of the openings generated in the membrane is tightly in contact with the outer perimeter of the capillary 8, so that the sealing rings 35 explained above, are not needed.

The division into several chambers 71 has the advantage that simultaneous with the use of a single supply vessel 7, several measurements can be carried out, whereby the used aperture holder 10 is divided by corresponding separating walls 72 likewise into several blood sampling areas 73, and where at least one part 5' having an aperture 5 and a separate capillary are allocated to each of these chambers 73, as is shown in FIG. 11.

The advantage of the division of the supply vessel 7 into several chambers 71, consists in the fact that several measurements can be carried out at the same time, which results in a considerably savings in time, and secondly, that every chamber 71 has less volume, so that when pipetting the same quantity of blood, the level of the blood in this chamber is greater than in a blood chamber without separating walls. This has the advantage that less blood is needed to carry out a measurement and that the capillary need not be run down to the base of the supply vessel 7. Preferably, when taking measurements of children's blood, where often very small quantities of blood are available per measurement, e.g. 0.5 mL, in the supply vessel 7 provided with separating walls 70, only one chamber 71 will be filled, so that even for the smaller available quantity of blood, a higher blood level in the chamber will result. In a comparatively large supply vessel 7 without separating walls 70, for a blood quantity of 0.5 mL, a measurement will be very difficult, because the level in the supply vessel is very low, so that the intake of the entire quantity of blood distributed in the large supply vessel into a capillary would hardly be possible.

Figure 1:
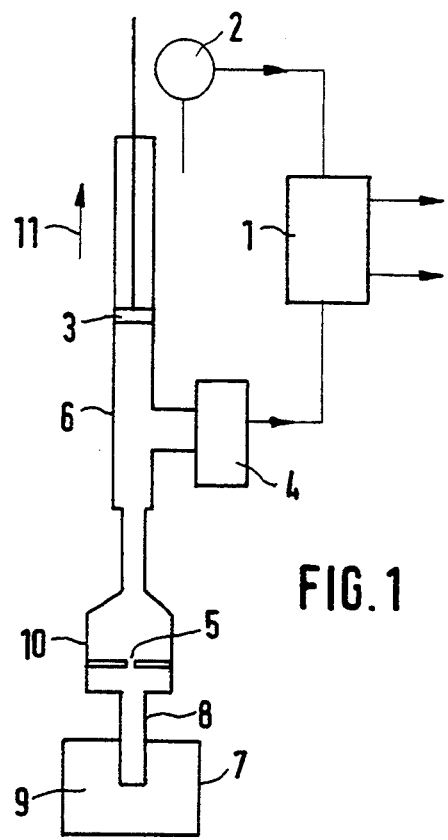
FIG. 1 is a schematic representation of a known measuring device to explain the handling of the supply vessel and of the capillary joined to the aperture holder.

At the upper end, the aperture holder 10 is sealed by a membrane section 76 into which the connecting lines to the cylinder 6 (FIG. 1) can be tightly inserted. Preferably the membrane unit 76 consists of a rubber or soft plastic material into which the connecting lines can be tightly inserted, whereby the resulting holes will close again upon removal of the connecting lines as a result of the elasticity of the rubber or soft plastic material. The separating wall 72 or the separating walls 72 extend up to the membrane section 76, so that every blood sampling chamber 73 is sealed off. By means of the stated connecting lines, a vacuum will be generated in the chambers.

In a supply vessel with only one chamber, for example, for taking of one measurement, for which only a small quantity of blood is available, the level of the blood in the supply vessel 7 can be increased by inserting a ring 77 into the supply vessel 7 so that the ring will reduce the volume of the supply vessel in the lower region.

If this ring 77 is made of a magnetic material, it can also be used to invert or to mix the blood in the supply vessel 7. To do this it is necessary merely to attach an additional, preferably ring-like magnet 78, to the outer side of the supply vessel 7 and to set it in rotation with a drive mechanism (not shown).

In order to achieve a particularly good mixing of the blood in the supply vessel 7 during the rotation of the installed ring 77, the installed ring 77 can have on its inner surface, inward protruding, preferably propeller-like or blade-shaped protrusions 79 or similar features, that form a type of agitator unit.

The aperture holder 10 can be lockable to the supply vessel 7 in the manner described above.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A device for the safe removal of blood from a supply vessel using an aperture holder having a capillary for removing the blood from the supply vessel via a suction operation, comprising:

a supply vessel having an opening therein for accepting blood;

an aperture holder defining an aperture and having a depending first capillary positioned for insertion into the opening of the supply vessel;

a cover unit sealing the opening of the supply vessel, the cover unit including a region through which the capillary is insertable into the supply vessel while the cover unit seals the opening of the supply vessel; and a locking means for locking the supply vessel and the cover unit to the aperture holder and preventing the supply vessel and the aperture holder from being separated, wherein the locking means includes a ventilation gap located in a space between the opening in the supply vessel and the cover unit adapted to allow ambient air to enter the supply vessel when blood is withdrawn through the capillary, which facilitates removal of the blood, while also being adapted to prevent blood from escaping therethrough.

2. A device according to claim 1, wherein the region through which the capillary is inserted is formed by an opening located in the cover unit.

3. A device according to claim 2, wherein the region through which the capillary is inserted is comprised of a foil.

4. A device according to claim 3, wherein the foil has a handle or grasping region protruding beyond an edge region of the cover unit.

5. A device according to claim 1, wherein the region through which the capillary is inserted comprises a thin-wall region in the cover unit that can be pierced by the capillary or a piercing means.

6. A device according to claim 5, wherein the region includes a central region located at a center of the cover unit.

7. A device according to claim 6, wherein the central region comprises a cross slit or a circle.

8. A device according to claim 1,
   wherein the cover unit includes a film hinge, the cover unit and the film hinge formed as a single piece, and
   wherein the cover unit is permanently attached using the film hinge to the supply vessel while the capillary is inserted through the region of the cover unit into the supply vessel.

9. A device according to claim 1, wherein the locking means comprises at least one protrusion mounted to the aperture holder and at least one recess provided in the supply vessel and wherein the at least one protrusion includes a rod protruding beyond the side of the aperture holder facing the supply vessel.

10. A device according to claim 9, wherein a plurality of protrusions are distributed uniformly along a perimeter of the aperture holder.

11. A device according to claim 9, wherein the at least one recess is provided in a wall of the supply vessel or in a portion of the cover unit.

12. A device according to claim 9, wherein the at least one recess is formed by a shoulder that is located in a transition region between a wall of the supply vessel and the cover unit.

13. A device according to claim 1, wherein the capillary and the aperture holder are of single-part integral design.

14. A device according to claim 1, wherein the aperture holder is sealed on a side facing away from the supply vessel by a seal part that has a central opening.

15. A device according to claim 14, wherein the seal part is an adhesive foil.

16. A device according to claim 1, wherein the aperture holder with the capillary and the supply vessel, are a single, disposable piece.

17. A device according to claim 1, wherein the supply vessel including a bottom is subdivided by a first separating wall into first and second chambers containing first and second blood samples respectively, and the first separating wall extends from the bottom of the supply vessel up to the opening in the supply vessel, and wherein the aperture holder includes a second capillary and is subdivided by a second separating wall into first and second blood holding chambers, wherein the first capillary draws the first blood sample from the first chamber of the supply vessel into the first blood holding chamber and the second capillary draws the second blood sample from the second chamber of the supply vessel into the second blood holding chamber.

18. A device according to claim 17, wherein the cover unit includes a region corresponding to each chamber in the supply vessel when the cover unit seals the supply vessel.

19. A device according to claim 18, wherein the second separating wall in the aperture holder extends up to a membrane part on the side of the aperture holder facing away from the supply vessel, to seal the first and second blood holding chambers, and a connection line is tightly inserted through the membrane part in each blood holding chamber to generate a vacuum therein, thus producing a hole in the membrane part corresponding to each blood holding chamber which closes after removal of the connecting line due to elasticity of the membrane part.

20. A device according to claim 19, wherein the membrane part is made of a rubber or soft plastic material.

21. A device according to claim 1, wherein the supply vessel is divided into two or four chambers.

22. A device according to claim 1, wherein the supply vessel is divided into multiple chambers holding blood and an insertion ring that reduces the volume of the supply vessel, is set into the chambers of the supply vessel.

23. A device according to claim 22, wherein the insertion ring rotates in the supply vessel.

24. A device according to claim 23, wherein the insertion ring comprises of a magnetic material and a rotating magnetic device is provided that surrounds the supply vessel externally in the region of the insertion ring.

25. A device according to claim 24, wherein the magnetic device is a ring-like magnet.

26. A device according to claim 22, wherein the insertion ring has protrusions on its inside surface, through which the mixing of blood contained in the chambers is promoted when turning the insertion ring.

27. A device according to claim 1, further comprising a sealing element disposed between the aperture holder and the supply vessel, and forming a tight joint between the aperture holder and the supply vessel while maintaining the ventilation gap to prevent the blood from exiting the device.

* * * * *